United States Patent
Philipps et al.

(10) Patent No.: US 9,357,784 B2
(45) Date of Patent: Jun. 7, 2016

(54) METHOD FOR PHYSICAL PLANT TREATMENT

(75) Inventors: André Philipps, Regensburg (DE);
Manuel Czech, Donaustauf (DE);
Michael Saefkow, Weinsberg (DE)

(73) Assignee: SIMPLY WATER GMBH, Regensburg (DE)

( * ) Notice: Subject to any disclaimer, the term of this patent is extended or adjusted under 35 U.S.C. 154(b) by 1012 days.

(21) Appl. No.: 13/388,566

(22) PCT Filed: Aug. 3, 2010

(86) PCT No.: PCT/EP2010/061298
§ 371 (c)(1),
(2), (4) Date: Sep. 12, 2012

(87) PCT Pub. No.: WO2011/015583
PCT Pub. Date: Feb. 10, 2011

(65) Prior Publication Data
US 2013/0004366 A1 Jan. 3, 2013

(30) Foreign Application Priority Data
Aug. 3, 2009 (DE) .......................... 10 2009 028 188

(51) Int. Cl.
*A61L 2/03* (2006.01)
*A01N 59/00* (2006.01)

(52) U.S. Cl.
CPC ...................................... *A01N 59/00* (2013.01)

(58) Field of Classification Search
CPC .................................. A61L 2/03; A61L 2/035
USPC ......................................................... 422/22
See application file for complete search history.

(56) References Cited

FOREIGN PATENT DOCUMENTS

| DE | 102007017502 | | 10/2008 |
|---|---|---|---|
| JP | 08056523 | A | 3/1996 |
| JP | 08109107 | A | 4/1996 |
| JP | 2000015258 | A | 1/2000 |
| JP | 2000016903 | A | 1/2000 |
| JP | 2002104908 | A | 4/2002 |
| KR | 20050008480 | A | 1/2005 |
| KR | 20090058268 | A | 6/2009 |
| WO | WO2008/101364 | A2 | 8/2008 |

OTHER PUBLICATIONS

International Search Report for related PCT Application No. PCT/EP2010/061298, dated Oct. 4, 2010.
Written Opinion for related PCT Application No. PCT/EP2010/061298, dated Oct. 4, 2010.
International Preliminary Report on Patentability for related PCT Application No. PCT/EP2010/061298, dated Feb. 16, 2012.

*Primary Examiner* — Sean E Conley
(74) *Attorney, Agent, or Firm* — McCarter & English, LLP; Steven G. Davis; Wei Song

(57) ABSTRACT

The present invention relates to a method for physical plant treatment by means of electrostatic charge, wherein a transfer of the electrostatic charge takes place via water treated by way of an influence process, wherein the water comprises water clusters having an electron deficit due to the treatment by means of an influence process, wherein the water treated by means of an influence process can be obtained by the following process steps:
  Introducing the water to be treated into a galvanic element,
  Aligning the charges and free electrons in the electric field,
  Separating the charges by motion and by the influence resulting therefrom and
  Collecting and discharging the de-electronized positively-charged fraction.
The method for physical plant treatment allows comprehensive and effective control of fungal diseases, simultaneously avoiding toxicological impact on the environment.

20 Claims, No Drawings

METHOD FOR PHYSICAL PLANT TREATMENT

This application is a 35 U.S.C. §371 national stage filing of International Application No. PCT/EP2010/061298, filed Aug. 3, 2010, which claims priority under 35 U.S.C. §119 to Germany Patent Application Serial No. 102009028188.6, filed Aug. 3, 2009. The entire contents of each of the aforementioned applications are incorporated herein by reference in their entirety.

The present invention relates to a method for physical plant treatment by means of electrostatic charge, wherein a transfer of the electrostatic charge takes place via water treated by way of an influence process.

In order to control diseases in plants, the state of the art uses various methods or substances with a chemical or biological action. Preference is in this case given to substituted heterocyclics, such as picoline amide derivatives. Furthermore, fenbutatin oxide, pyrimethanil, fludioxonil, cyprodinil or fenhexamid are used. Some of these known compounds, however, have the disadvantage that they represent toxic products, which precludes or, at least, substantially limits any use of these compounds in agriculture for eradicating phytopathogenic diseases of crop plants. Others of these compounds are derived from fermentation residues and have relatively complex chemical structures. The production and isolation of these compounds therefore still involves complex, expensive process steps, often making it uneconomical to prepare them industrially or to commercialise them. In addition, the launch of such compounds in plant protection usually requires an extensive and elaborate approval process.

Based on the aforegoing, it is the object of the present invention to provide a method which controls the diseases of plants effectively, which poses no toxicological risk and can therefore be used safely in the crop plant sector, in particular in agriculture.

This object is attained by the feature of patent claim 1. Advantageous embodiments and further developments, which may be used individually or in combination, form the subject of the subsidiary claims.

The present invention attains the given object in that it provides a method for physical plant treatment by means of electrostatic charge, wherein a transfer of the electrostatic charge takes place via water having been treated by way of an influence process, wherein the water comprises water clusters having an electron deficit due to the treatment by way of the influence process, and wherein the water treated by way of the influence process can be obtained by the following process steps:

Introducing the water to be treated into a galvanic element,
  Aligning the charges and free electrons in the electric field,
  Separating the charges by motion and by the influence resulting therefrom and
  collecting and discharging the de-electronised positively-charged fraction.

This attains a substantial improvement over the prior art. The method according to the invention effectively controls diseases, but is at the same time safe for the environment. The method according to the invention for physical plant treatment has no toxic effects on animals, plants or even consumers present in the environment. The method gives rise to oxidative products at such an extremely low level that the effectiveness must be based on a different effect. It may be assumed that the effectiveness of water treated as described above is caused by the excitation of the water molecule itself. The water molecules are present in a cluster structure state, formed as a result of the electrostatic dipole structure of the water molecules. By performing an influence, water molecules are electrically discharged and the charge carriers generated in the cluster structure are stabilised by constant exchange (Grotthus mechanism). As a result, the so electrically-discharged water can act as a disinfectant, because it is able to denature cellular structures or to destroy the electron transport mechanisms of micro-organisms irreversibly. This is one of the reasons why no resistance is formed in the micro-organisms or fungi.

Due to the electron deficit brought about in this manner, the water clusters (co-bonded water molecules resulting from the magnetic effect of the water molecule dipole) are electrically discharged. Positively-charged water clusters are formed which act as electron acceptors, so-called electron deficit. The latter is satisfied by an electron donor, e.g. any single-cell life form.

In a preferred embodiment, the effect of the method for physical plant treatment can be erased by treating the solution with X-rays. It was possible to observe that water treated by an influence process, which was dispatched by air, had no effect. Oxidative intermediates that are formed, for example, by electrolysis are insensitive to X-rays. X-ray treatment brings about a strong electron infusion. It can be assumed that the electron deficiency, the so-called electron deficit, is counteracted by the X-ray treatment. Water treated in this manner no longer exhibits any physical effectiveness. Thus, sensitivity of the water to X-rays may serve as proof of an electron deficit. Only water which responds to treatment with X-rays by a loss of effectiveness acts due to electron deficit.

It has proved advantageous, if the method for physical plant treatment has a fungicidal and/or bactericidal and/or virucidal and/or sporicidal effect. This allows attaining a particularly comprehensive and effective physical plant treatment.

In a further preferred embodiment the water contains sodium chloride. The addition of sodium chloride facilitates the influence, since the conductivity of the water can be adjusted.

In a particularly preferred embodiment, the influence can be performed at a current density ranging from 0.5 to 10 W per $cm^2$.

It has proved particularly advantageous, if the method for physical plant treatment is used for the control of plant diseases.

In this context, it is particularly advantageous, if the process is used for controlling fungal diseases and/or viral diseases and/or bacterial diseases and/or spore diseases in plants.

The method is most particularly advantageous in the control of *Botrytis* and/or blight. *Botrytis* (*Botryotinia*) is a cosmopolitan genus of the sac fungi (*Ascomycota*). All species are significant plant pests, a particularly known representative being grey mould rot (*Botrytis cinerea*) with a very large range of host plants. *Botrytis* species live as parasites and in the process inject an apoptosis of the infected cells in the infected tissue of infected plants. This results in a progressive degeneration of the tissue. *Botrytis* poses a risk to human health, due, in particular, to its high allergenic potential. The genus ranks among the most important ones of all genes amongst mould fungi. Blight is caused, in particular, by *Phytophthora infestans*, a type of protist from the group of egg-shaped fungi (*Oomycota*). This pathogen is highly-specialised with regard to its hosts. If this parasite infects tomatoes, it is referred to as leaf mould or brown rot; if, on the other hand, it infects potatoes, it is referred to as blight or late blight. In the case of potatoes, the infection results in significant yield losses, which can destroy up to 20% of an average yield. In the mid-40s of the $19^{th}$ century a *Phytophthora* epidemic destroyed nearly the entire potato crop in Ireland. This brought about the Great Famine in Ireland, which killed more than 1 million of the Irish population of then over 8 million inhabitants. The two described diseases can be controlled effectively and comprehensively by employing the method. The key advantage here is that the method used is toxicologically completely safe.

It is furthermore particularly advantageous, if the method is used as preventive or curative control of phytopathogenic organisms, which is characterised in that an amount of water treated by way of the influence method is applied to the plant seeds and/or plant leaves and/or plant fruit and/or to the soil in which the plants grow and/or are intended to grow.

In this context, it is particularly advantageous, if the method is used for preventive and/or curative control of phytopathogenic organisms in diseases, caused by fungi and/or viruses and/or bacteria and/or spores.

Further advantages and embodiments of the invention are illustrated below with reference to working examples.

The method according to the invention for physical plant treatment by means of electrostatic charge is performed as follows. For a better understanding, the physical basics are also briefly described.

The method is based on the property of micro-organisms to carry negative charges.

Based on the generation of an influence in an electric field (electrostatic induction), charge carriers are separated in water and negative charge carriers are discharged to a certain extent. Finally, the fraction with a positive electrostatic charge is captured. In this way the positively-charged charge carriers can be passed on, so that eventually they can be applied to a substance contaminated by micro-organisms.

The contact with micro-organisms results in a charge exchange in the form of electric shock. Within fractions of a second, the pore function of the single-cell organism is irreversibly damaged. The micro-organism is then no longer viable. Killing the micro-organism is thus based on triggering an electric shock, which occurs by a transfer of electrostatic charge.

As is known, water molecules are dipoles, whose oppositely-charged ends attract one another. Thus, dimers are formed initially, which, since 1961, are designated as 'Zundel' cations. These aggregate into larger agglomerates, the so-called clusters. Clusters are a subset of van-der-Waals bodies, as these are held together by London-van-der-Waals-forces. The size of the clusters, in this context, depends inter alia on the location in the water, where they are to be found. At the surface, they are mostly broadly-spread out micro-clusters of 2 to 12 molecules, the deeper the clusters are positioned, the more they increase in size. One distinguishes between "Small Clusters" of 10 to 100, "Large Clusters" from 100 to 1000 and "Small Droplets" or "Crystals" consisting of more than 1000 water molecules.

An essential feature of van-der-Waals-clusters is their property that the electrons are no longer bound to the orbitals and shells of their parent atoms/molecules. They are randomly distributed in the cluster according to the Schrödinger-equation (1926) and can stray freely within the cluster composite. In solid van-der-Waals-clusters (such as, e.g. metals) they are referred to in their entirety as electron gas, responsible, for example, for the electrical conductivity of metals.

By the process described below, electrons are extracted from the water. An electron deficit in the clusters (incorrectly referred to as proton) does not result in instability of the cluster structure, but is compensated for by the Grotthus-mechanism (1820) by so-called proton hopping.

On the issue of the interactions between water and the electric charge, there is a well-known experiment, in which the deflection of a thin water jet through an electrostatically-charged object can be visualised. The dipoles and charges in the water clusters become aligned by the electrostatic charge of the object. As opposing charges attract each other, the jet is deflected toward the charged object.

The method according to the invention is based on electrostatic induction or influence. In this context, a movement in the electric field results in the separation of charges, the influence.

The extraction of the water treated by way of the influence process for performing a physical plant treatment by way of electrostatic charge is obtained as follows:

Cluster-water whose conductivity is adjusted to a desired value by adding common salt, flows in an electrostatic field (stationary electric field), which is formed by an anode and a cathode.

In a first step, the charges and free electrons are aligned in the electric field.

In a second step, due to the movement and subsequent influence, the charges are separated and discharged.

The fraction with a deficit of electrons is removed and collected as the concentrate to be used, the result being a de-electronised (positively-charged) fraction.

This yields electrostatically positively-charged water. It has a high demand for filling the uncharged positions in the clusters. Contact with electron-rich surfaces results in an electric shock that brings about charge neutralisation.

Measurement and detection of the positive, electrostatic charge:

The problem is that currently no measuring method exists to measure a positive electrostatic charge in the water. For lack of better methods and for historical reasons, one therefore makes do with the DPD-method, i.e. by measuring the oxidative change of the dye DPD by electron withdrawal in the oxidant to be measured. Depending on the measuring instrument used, the "oxidising power" is expressed as the concentration of hydrogen peroxide ($H_2O_2$), ozone ($O_3$) or free chlorine. "Chlorine measurement" is the most widely-used method. It currently also serves as a simple on-site method to determine and adjust concentrations.

DPD (N,N-diethyl-1,4-phenylendiamine) is a colour complex, which changes from colourless to red with the release of electrons and then again from red to colourless with the reintroduction of electrons. No chemical bonding of the dye with chlorine, ozone or hydrogen peroxide takes place, but the latter merely withdraw electrons due to their oxidant properties.

The water treated by way of the influence process in the method for physical plant treatment by electrostatic charge, has an electrostatic charge, in terms of this measuring method, which corresponds to an equivalent of free chlorine of about 150 ppm.

As the method is remotely similar to known electrolysis processes, the intention was to investigate whether the withdrawal of electrons gives rise to unpaired electrons, typical for electrolysis, i.e. radical formation. For this purpose, molecules or ions with unpaired electrons in activated water were searched for by way of the electron-spin-resonance method. Electron-spin-resonance (ESR) allows detecting and quantifying molecules or ions with non-zero total electron spin. The method is also known as EPR (Electron Paramagnetic Resonance).

By the direct detection method no unpaired electrons could be detected. The amount of unpaired electrons was below the detection threshold of $10^{10}$ spin/Gauss.

It was subsequently attempted to detect unpaired electrons by using two so-called spin traps. DMPO and PBN were used. Those substances respond to molecules having unpaired electrons and yield corresponding resonances.

With the spin traps as well, it was not possible to detect any unpaired electrons.

The effectiveness of the method for physical plant treatment is now elucidated by way of the following example.

EXAMPLE 1

In-Vivo Test on *Botrytis cinerea* (Grey Mould in Cucumbers)

An active substance testing concentration of 50% is obtained by diluting the water for physical plant treatment, treated by way of the influencing method, with water so that the desired concentration of the active ingredient is obtained. Cucumber plants (variety: Marketer) in seedling trays, which were sown on a peat soil-pozzolana substrate (50/50) and cultured at 18 to 20° C., were treated in the cotyledon stage Z11 in that they were sprayed with the above-described water treated by way of the influence method. Plants used for control were sprayed with an aqueous solution containing no water treated by the influence method.

After 24 hours, the plants are inoculated in that drops of an aqueous suspension of *Botrytis cinerea* spores (150 000 spores per ml) are deposited on the upper leaf surface. The spores originate from a 15-day-old culture and are suspended in a nutrient solution having the following composition:
20 g/l gelatine
50 g/l cane sugar
2 g/l $NH_4NO_3$
1 g/l $KH_2PO_4$.

The inoculated cucumber plants are left 5/7 days in a climatic chamber at 15 to 11° C. (day/night) and 80% relative humidity.

5/7 days after inoculation an evaluation is performed in comparison with the control plants. Under these conditions, good protection (at least 50%) in the water is observed with a 50% concentration of the water treated by the influencing method.

EXAMPLE 2

In-vivo Test of *Phytophthora infestans* (Late Blight of Potato)

In a field trial, water treated according to the invention for the prevention or treatment of late blight caused by *Phytophthora infestans* in early potatoes was investigated. For this purpose, the treatment with a copper-containing solution known from organic farming was compared with two dilutions of influence-treated water. The water according to the invention was applied to the plants in 20% or 50% diluted concentrations, the copper-containing solution (Cuprozin® liquid, containing 460.6 g/l copper hydroxide, equivalent to 300 g/l pure copper) having been used in such a manner that the conventional 200-500 g of copper were applied per hectare.

80 early potato plots were treated with different preparations and tested and assessed both one week before harvest and during harvest in terms of their contamination with late blight.

The untreated plots were seriously affected as early as one week before harvest and during harvest; the plots contained a plurality of major centres of infection ("honeycombs") of late blight.

The plots treated with the copper-containing solution showed basically a similar blight infection as the plots treated with the 20 percent-diluted water according to the invention: both one week before harvest as well as during harvest merely a single first late blight infection was observed, where individual leaves of the plants were infected.

The lowest late blight infestation was seen in those early potato plots, which had been treated with 50-percent-diluted water according to the invention. In this case, the plots were still completely free from infestation one week prior to harvest; only during harvest did the plants exhibit a single first infestation in the form of individual, infected plant leaves.

On further examination, it could furthermore be detected that areas that had been treated with copper according to the organic farming practice, showed 11% of problematic late blight infestation. In this case, 7% were in the form of plant infestation of the leaves or stems, while 4% represented "honeycombs" affected by late blight.

Areas treated with water obtained by the influence process, showed an 8% problematic late blight infestation. However, no honeycombing could be detected under these treatment conditions.

The field trials in early potatoes show that treatment of late blight with 20-percent water obtained according to the influence process can replace treatment with a copper-containing preparation.

The use of a 50% dilution of the water produced according to the patent is even superior to late blight control by copper treatment, as evidenced by a generally lower infestation as well as by higher yields associated therewith.

Both application examples demonstrate that the method of physical plant treatment permits a comprehensive and effective control of diseases in plants, thereby simultaneously avoiding toxicological impact on the environment.

The invention claimed is:

1. Method for physical plant treatment by means of electrostatic charge comprising:
    i) treating water by means of an influence process, wherein the treated water comprises water clusters having an electron deficit, and
    ii) spraying or applying the treated water from step i) to the physical plant, thereby resulting in a transfer of the electrostatic charge from the treated water to the physical plant; wherein the water treated by means of the influence process can be obtained by the following process steps:
    introducing the water to be treated into a galvanic element,
    aligning the charges and free electrons in the electric field,
    separating the charges by motion and by the influence resulting therefrom, and
    collecting and discharging the de-electronised positively-charged fraction.

2. Method for physical plant treatment by means of electrostatic charge according to claim 1, wherein the effect of the method is erasable by treatment of the water with X-rays.

3. Method for physical plant treatment by means of electrostatic charge according to claim 1, wherein the method has a fungicidal and/or bactericidal and/or virucidal and/or sporicidal effect.

4. Method for physical plant treatment by means of electrostatic charge according to claim 1, wherein the water contains sodium chloride.

5. Method for physical plant treatment by means of electrostatic charge according to claim 1, wherein the influence process can be performed at a current density of from 0.5 to 10 W per cm2.

6. Method for physical plant treatment by means of electrostatic charge according to claim 1, wherein the method is used for the control of fungal diseases and/or viral diseases and/or bactericidal diseases and/or spore diseases.

7. Method for physical plant treatment by means of electrostatic charge according to claim 1, wherein the method is used for the control of fungal diseases in plants.

8. Method for physical plant treatment by means of electrostatic charge according to claim 6, wherein the fungal disease is *Botrytis* and/or blight.

9. Method for the preventive and/or curative control of phytopathogenic organisms, comprising:
applying an effective, non phytotoxic quantity of water treated by means of an influence process according to claim 1 to plant seed and/or plant leaves and/or plant fruit and/or to the soil, in which the plants are growing and/or are supposed to grow.

10. Method for the preventive and/or curative control of phytopathogenic organisms according to claim 9, wherein the pathogens are fungi and/or viruses and/or bacteria and/or spores.

11. Method for physical plant treatment by means of electrostatic charge according to claim 1, wherein the method has no toxic effects on animals, plants or consumers present in the environment.

12. Method for physical plant treatment by means of electrostatic charge according to claim 1, wherein the water used is electrostatically positively-charged and, when in contact with electron-rich surfaces, results in an electric shock, causing charge exchange.

13. Method for physical plant treatment by means of electrostatic charge according to claim 1, wherein the water used contains an electrostatic charge which corresponds to an equivalent of free chlorine of about 150 ppm.

14. Method for physical plant treatment by means of electrostatic charge according to claim 2, wherein the method has a fungicidal and/or bactericidal and/or virucidal and/or sporicidal effect.

15. Method for physical plant treatment by means of electrostatic charge according to claim 2, wherein the water contains sodium chloride.

16. Method for physical plant treatment by means of electrostatic charge according to claim 2, wherein the influence process can be performed at a current density of from 0.5 to 10 W per cm2.

17. Method for physical plant treatment by means of electrostatic charge according to claim 7, wherein the fungal disease being *Botrytis* and/or blight.

18. Method for physical plant treatment by means of electrostatic charge according to claim 2, wherein the method has no toxic effects on animals, plants or consumers present in the environment.

19. Method for physical plant treatment by means of electrostatic charge according to claim 2, wherein the water used is electrostatically positively-charged and, when in contact with electron-rich surfaces, results in an electric shock, causing charge exchange.

20. Method for physical plant treatment by means of electrostatic charge according to claim 2, wherein the water used contains an electrostatic charge which corresponds to an equivalent of free chlorine of about 150 ppm.

* * * * *